United States Patent
Habermann et al.

(10) Patent No.: US 6,534,288 B1
(45) Date of Patent: Mar. 18, 2003

(54) C PEPTIDE FOR IMPROVED PREPARATION OF INSULIN AND INSULIN ANALOGS

(75) Inventors: Paul Habermann, Eppstein (DE); Johann Ertl, Eppstein (DE); Johannes Meiwes, Idstein (DE); Gerhard Seipke, Hofheim (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 09/676,787

(22) Filed: Oct. 2, 2000

(30) Foreign Application Priority Data

Oct. 2, 1999 (DE) .......................................... 199 47 456

(51) Int. Cl.⁷ .............................................. C12N 15/00
(52) U.S. Cl. .................. 435/69.4; 435/69.1; 435/320.1; 435/325; 435/252.3; 530/303; 530/350; 536/23.51
(58) Field of Search ................................ 530/303, 350; 435/69.1, 320.1, 325, 252.3, 69.4; 536/23.51

(56) References Cited

U.S. PATENT DOCUMENTS 4,430,266 A   2/1984   Frank

FOREIGN PATENT DOCUMENTS

| EP | 0 704 527 A2 | 4/1996 |
| EP | 0 821 006 A2 | 1/1998 |
| EP | 0 885 961 A1 | 12/1998 |

OTHER PUBLICATIONS

Kaufmann, Biochem. J. 310: 869–874, 1995.*
Schmidt et al., "Temperature–induced production of recombinant human insulin in high–cell density cultures of recombinant *Escherichia coli*," Journal of Biotechnology, 1999, pp. 71–83, vol. 68, No. 1, Elsevier.
Steiner et al., "The Role of Prohormone Convertases in Insulin Biosynthesis: Evidence for Inherited Defects in their Action in Man and Experimental Animals," Diabetes & Metabolism, 1996, pp. 94–104, vol. 22, No. 2.
Vollenweider et al., "Processing of Proinsulin by Furin, PC2, and PC3 in (Co)Transfected COS (Monkey Kidney) Cells," Diabetes, Sep. 1995, pp. 1076–1080, vol. 44.
Yanagita et al., "Processing of Mutated Proinsulin with Tetrabasic Cleavage Sites to Mature Insulin Reflects the Expression of Furin in Nonendocrine Cell Lines," Endocrinology, 1993, pp. 639–644, vol. 133, No. 2.

\* cited by examiner

*Primary Examiner*—Lorraine Spector
*Assistant Examiner*—Eliane Lazar-Wesley
(74) *Attorney, Agent, or Firm*—Heller Ehrman White & McAuliffe, LLP

(57) ABSTRACT

The invention relates to a precursor of human insulin or of an insulin analog of the formula I:

$$\text{Fus-B(1-30)-RDVP-}Y_n\text{-A(1-21)} \qquad \text{(I);}$$

wherein

Fus is an optionally present fusion portion;

B(1-30) is a B chain of human insulin,

Y is an amino acid chain which terminates with a basic amino acid at the C terminus;

n is from 2 to 50 and indicates the length of the amino acid chain Y; and

A(1-21) is an A chain of human insulin, and the A chain and/or the B chain can be modified by amino acid substitution, deletions and/or additions. The present invention also provides DNA coding for the above precursors, preparation and use of the instant precursors and DNA, and a process for preparing human insulin or an insulin analog.

14 Claims, No Drawings

SEQUENCE LISTING

<160> NUMBER OF SEQ ID NOS: 13

<210> SEQ ID NO 1
<211> LENGTH: 87
<212> TYPE: DNA
<213> ORGANISM: Homo sapiens

<400> SEQUENCE: 1
cgcgatgttc ctcaggtgga gctgggcggg ggccctggcg caggcagcct gcagcccttg     60
gcgctggagg ggtccctgca gaagcgc                                         87

<210> SEQ ID NO 2
<211> LENGTH: 29
<212> TYPE: PRT
<213> ORGANISM: Homo sapiens

<400> SEQUENCE: 2

Arg Asp Val Pro Gln Val Glu Leu Gly Gly Gly Pro Gly Ala Gly Ser
1               5                   10                  15

Leu Gln Pro Leu Ala Leu Glu Gly Ser Leu Gln Lys Arg
            20                  25

<210> SEQ ID NO 3
<211> LENGTH: 45
<212> TYPE: DNA
<213> ORGANISM: Artificial Sequence
<220> FEATURE:
<223> OTHER INFORMATION: Primer PINT358fIII

<400> SEQUENCE: 3
cccaagaccc gcgatgttcc tcaggtggag ctgggcgggg gccct                     45

<210> SEQ ID NO 4
<211> LENGTH: 40
<212> TYPE: DNA
<213> ORGANISM: Artificial Sequence
<220> FEATURE:
<223> OTHER INFORMATION: Primer PINT358revII

<400> SEQUENCE: 4
cagctccacc tgaggaacat cgcgggtctt gggtgtgtag                           40

<210> SEQ ID NO 5
<211> LENGTH: 31
<212> TYPE: DNA
<213> ORGANISM: Artificial Sequence
<220> FEATURE:
<223> OTHER INFORMATION: Primer Salforward

<400> SEQUENCE: 5
tacacacccg agacccgcga tgttcctcag g                                    31

<210> SEQ ID NO 6
<211> LENGTH: 32
<212> TYPE: DNA
<213> ORGANISM: Artificial Sequence
<220> FEATURE:
<223> OTHER INFORMATION: Primer 329rev

<400> SEQUENCE: 6
cctgaggaac atcgcgggtc tcgggtgtgt ag                                   32

<210> SEQ ID NO 7
<211> LENGTH: 91
<212> TYPE: PRT
<213> ORGANISM: Artificial Sequence
<220> FEATURE:
<223> OTHER INFORMATION: Fusion protein encoded by pINT362d

<400> SEQUENCE: 7

Met Ala Thr Thr Ser Thr Gly Asn Ser Ala Arg Phe Val Lys Gln His
1               5                   10                  15

Leu Cys Gly Ser His Leu Val Glu Ala Leu Tyr Leu Val Cys Gly Glu
            20                  25                  30

Arg Gly Phe Phe Tyr Thr Pro Glu Thr Arg Asp Val Pro Gln Val Glu
        35                  40                  45

Leu Gly Gly Pro Gly Ala Gly Ser Leu Gln Pro Leu Ala Leu Glu
    50                  55                  60

Gly Ser Leu Gln Lys Arg Gly Ile Val Glu Gln Cys Cys Thr Ser Ile
65                  70                  75                  80

Cys Ser Leu Tyr Gln Leu Glu Asn Tyr Cys Asn
                85                  90

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide 140drev used as antisense
      primer

<400> SEQUENCE: 8
aaaggtcgac tattagccgc agta                                          24

<210> SEQ ID NO 9
<211> LENGTH: 3
<212> TYPE: PRT
<213> ORGANISM: Artificial Sequence
<220> FEATURE:
<223> OTHER INFORMATION: Amino acid encoded by 140drev antisense primer

<400> SEQUENCE: 9

Gly Cys Tyr
1

<210> SEQ ID NO 10
<211> LENGTH: 13
<212> TYPE: PRT
<213> ORGANISM: Artificial Sequence
<220> FEATURE:
<223> OTHER INFORMATION: Amino acid encoded by reverse primer PINT349a

<400> SEQUENCE: 10

Val Gln Pro Val Asp Arg His His Thr Lys Pro Thr Tyr
1               5                   10

<210> SEQ ID NO 11
<211> LENGTH: 40
<212> TYPE: DNA
<213> ORGANISM: Artificial Sequence
<220> FEATURE:
<223> OTHER INFORMATION: Reverse primer PINT349a

<400> SEQUENCE: 11
cacctgagga acatcgcggt ggtgggtctt gggtgtgtag                         40

```
-continued

<210> SEQ ID NO 12
<211> LENGTH: 13
<212> TYPE: PRT
<213> ORGANISM: Artificial Sequence
<220> FEATURE:
<223> OTHER INFORMATION: Amino acid encoded by primer PINT349b

<400> SEQUENCE: 12

Pro Lys Thr His His Arg Asp Val Pro Gln Val Glu Leu
1               5                   10

<210> SEQ ID NO 13
<211> LENGTH: 40
<212> TYPE: DNA
<213> ORGANISM: Artificial Sequence
<220> FEATURE:
<223> OTHER INFORMATION: Primer PINT349b

<400> SEQUENCE: 13
acccaagacc caccaccgcg atgttcctca ggtggagctg                              40
```

C PEPTIDE FOR IMPROVED PREPARATION OF INSULIN AND INSULIN ANALOGS

CROSS-REFERENCE TO RELATED APPLICATIONS

The present invention claims the priority benefit, under 35 U.S.C. § 119, of Federal Republic of Germany Application No. 199 47 456.7, filed Oct. 2, 1999.

BACKGROUND OF THE INVENTION

1. Field of the Invention

The present invention relates to a synthetic derivative of the proinsulin C peptide. Proinsulin comprising this derivative has properties which are better in various ways than conventional monkey proinsulin, in particular the final yield of the particular insulin derivative is improved on recombinant preparation thereof.

2. Description of the Related Art

The number of patients with diabetes is continually increasing around the world. There is a proportionate increase in the demand for insulin or derivatives of insulin. Thus the object is to optimize the existing processes in relation to the yield of active ingredient. European patent EP-B1 0 489 780 proposes a process for preparing insulin or derivatives thereof. The vectors described therein are used to prepare human insulin with the plasmid pINT90d or else starting plasmids for constructing the plasmid pINT302d which is described in European patent application EP-A 0 821 006 and is used for preparing a His(B31) His(B32) Gly(A21)-insulin derivative, or to construct the vector pINT329d, which is described in European patent application EP-A 0 885 961 and is used for preparing the Lys(B3) Glu(B29)-insulin derivative.

SUMMARY OF THE INVENTION

The instant invention therefore provides a precursor of human insulin or a precursor of an insulin analog of the formula I:

$$Fus\text{-}B(1\text{-}0)\text{-}RDVP\text{-}Y_n\text{-}A(1\text{-}21) \qquad (I);$$

wherein
  Fus is an optionally present fusion portion;
  B(1-30) is a B chain of human insulin,
  Y is an amino acid chain which terminates with a basic amino acid at the C terminus;
  n is from 2 to 50 and indicates the length of the amino acid chain Y; and
  A(1-21) is an A chain of human insulin,
and the A chain and/or the B chain can be modified by amino acid substitutions, deletions and/or additions.

In one embodiment, $Y_n$ is amino acids 5 to 35 of a C peptide of human or monkey insulin.

In another embodiment, $Y_n$ is amino acids 11 to 35 of human insulin.

In another embodiment, the B chain of human insulin comprises: Lys(B3)Glu(B29).

In another embodiment, the B and A chains of human insulin comprise: His(B31)His(B32)Gly(A21).

The instant invention also provides DNA encoding for those precursors of the instant invention.

The instant invention also provides a vector comprising a DNA encoding for those precursors of the instant invention.

In one embodiment, the vector is an expression vector suitable for expression in a host cell, preferably *E. coli*.

The instant invention also provides for a host cell comprising a vector comprising a DNA encoding for those precursors of the instant invention. Preferably the host is *E. coli*.

The instant invention also provides for a process for preparing a precursor of the instant invention, comprising the steps of:
  a) introducing a DNA coding for the instant precursors into a vector;
  b) introducing the vector from (a) into a host cell;
  c) allowing the host cell to express the precursor into a culture supernatant; and
  d) isolating the precursor from the culture supernatant.

The instant invention also provides for a process for preparing DNA, comprising the steps of:
  a) producing a DNA from a cDNA of human or monkey insulin by PCR; and
  b) isolating said DNA;
wherein said DNA encodes a precursor of the instant invention.

The instant invention also provides for a process for preparing human insulin or an insulin analog, comprising the steps of:
  a) preparing a said precursors by the instant processes of the instant invention;
  b) forming disulfide bridges in the precursor by allowing the precursor from (a) to fold;
  c) optionally enzymatically cleaving the fusion portion Fus; and
  c) purifying the human insulin or the insulin analog.

DETAILED DESCRIPTION OF THE PREFERRED EMBODIMENT

It has now been found that particularly advantageous proinsulin derivatives are those of the formula I, $$Fus\text{-}B(1\text{-}30)\text{-}RDVP\text{-}Y_n\text{-}A(1\text{-}21) \qquad (I);$$

wherein
  Fus is an optionally present fusion portion of any suitable sequence;
  B(1-30) is the B chain of human insulin,
  Y is an amino acid chain which terminates with a basic amino acid at the C terminus;
  n is from 2 to 50 and indicates the length of the amino acid chain Y; and
  A(1-21) is the A chain of human insulin,
and wherein the A chain and/or the B chain can be modified by amino acid substitutions, deletions and/or additions. It is surprising in this connection that equal and mutually different advantages are observed depending on the composition of the insulin A or B chain.

Connection of the human B chain to the human A chain via the advantageous C peptide results in a proinsulin which behaves in terms of expression yield like wild-type proinsulin, but its enzymatic processing to insulin can be controlled more easily so that no disruptive traces of B chain extended by arginine are produced and have to be removed during preparation to give the pharmaceutical, causing losses of yield.

On connection of the B chain with a C-terminal di-histidine extension to the A chain of human insulin containing glycine in position A21 using the C peptide according to the invention there is found to be an expression yield which is about 20% higher than the yields which can be achieved with the plasmid pINT90d and a yield which is almost five times higher than observed with the plasmid pINT302d. In addition, control of the enzymatic processing is simplified in the same way as previously described.

On connection of a Lys(B3) Glu (B29)-modified B chain to the A chain of human insulin via the modified C peptide there is found to be improved folding properties of the proinsulin derivative compared with the proinsulin encoded by pINT329d. The yield of crude fusion protein is increased and reaches the same level as found with the plasmid pINT90d. In addition, control of the enzymatic processing is simplified.

A particularly advantageous embodiment of the novel C peptide is characterized by the following amino acid sequence: CGCGATGTTCCTCAGGTG-GAGCTGGGCGGGGGCCCTGGCGCAG-GCAGCCTGCAGCCCTTG RDVPQVELGGGP-GAGSLQPL
GCGCTGGAGGGGTCCCTGCAGAAGCGC (SEQ ID NO.: 1)

ALEGSLQKR (SEQ ID NO.: 2)

One of many possible DNA sequences coding for the indicated C peptide is likewise indicated.

One aspect of the invention is a precursor of human insulin or of an insulin analog of the formula I $$Fus\text{-}B(1\text{-}30)\text{-}RDVP\text{-}Y_n\text{-}A(1\text{-}21) \qquad (I);$$

wherein
Fus is an optionally present fusion portion of any suitable sequence;
B(1-30) is the B chain of human insulin,
Y is an amino acid chain which terminates with a basic amino acid at the C terminus;
n is from 2 to 50 and indicates the length of the amino acid chain Y; and
A(1-21) is the A chain of human insulin,
and wherein the A chain and/or the B chain can be modified by amino acid substitutions, deletions and/or additions, in particular where $Y_n$ is amino acids 5 to 35 of the C peptide of human or monkey insulin, preferably where $Y_n$ is amino acids 11 to 35 of human insulin.

Another aspect of the invention are precursors as described above, where the B chain of human insulin comprises the modifications Lys(B3) Glu(B29) or where the B and A chains of human insulin comprise the modifications His(B31) His(B32) Gly(A21).

The instant invention includes substitutions, additions, or deletions, of one or more amino acid residues of the claimed precursor of human insulin or precursor of an insulin analog of formula I.

Substitutional variants typically contain the exchange of one amino acid for another at one or more sites within the protein, and are designed to modulate one or more properties of the protein such as stability against proteolytic cleavage. Substitutions preferably are conservative, that is, one amino acid is replaced with one of similar shape and/or charge. Conservative substitutions are well known in the art and include, but are not limited to, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Addition variants contain fusion proteins such as those used to allow rapid purification of the protein and also can include hybrid proteins containing sequences from other proteins and polypeptides which are homologues of the protein.

Deletion variants, for example, lack one or more residues of the protein which are not essential for immunogenic activity or biological activity.

The present invention may also include such non-conservative additions, deletions or substitutions that do not destroy biological activity. Those persons skilled in the art, using established procedures to detect desired biological activity similar to insulin, can readily determine which amino acid residues may be added, deleted, or substituted, for example, by the measurement of biochemical activity of the polypeptides using conventional biochemical assays, such as in vitro assays detecting signal transduction in a biochemical pathway in which insulin is implicated. Alternatively, non-conservative substitutions may be made at positions in which, for example, alanine-scanning mutagenesis reveals some tolerance for mutation in that substitution of an amino acid residue with alanine does not destroy biological activity. The technique of alanine scanning mutagenesis is described by Cunningham and Wells, *Science*, 1989, 244:1081, and incorporated herein by reference in its entirety.

Well established preparatory techniques of the above-described variants are within the skill of the artisan. These procedures include, for example, conventional methods for the design and manufacture of DNA sequences coding for bacterial expression of the instant polypeptides, the modification of cDNA and genomic sequences by site-directed mutagenesis techniques, the construction of recombinant proteins and expression vectors, and bacterial expression of the polypeptides. These procedures are described, for example, in CURRENT PROTOCOLS IN MOLECULAR BIOLOGY, Ausubel et aL Eds. (John Wiley & Sons, New York, 1987).

The optional fusion portion includes those conventional fusion proteins that increase levels of expression, increases protein longevity, provides an efficient way of purification, or alternatively, are known selectable markers that are easily assayed for monitoring efficiency of both eucaryotic and procaryotic expression. Preferably, the instant fusion portion is protected against proteolytic degradation, allows a high yield of fusion protein, is easily soluble, does not impair folding of the fusion protein during conversion to mature insulin, allows enzymatic removal from the A- and B-chains in a one-pot reaction in which the C-chain is removed from the precursor, allows purification of the precursor by, for example, affinity chromatography, and is easily separated from insulin.

The artisan will readily recognize that those methods for preparing fusion proteins are well known in the art.

Examples of such fusion protein expression systems are the glutathione S-transferase system (Pharmacia, Piscataway, N.J.), the maltose binding protein system (NEB, Beverley, Mass.), the FLAG system (1B1, New Haven, Conn.), and the 6×His system (Qiagen, Chatsworth, Calif.). Some of these systems produce recombinant protein bearing only a small number of additional amino acids, which are unlikely to affect the antigenic ability of the recombinant protein. For example, both the FLAG system and the 6×His system add only short sequences, both of which are known to be poorly antigenic and which do not adversely affect folding of the protein to its native conformation. Other fusion systems produce proteins where it is desirable to excise the fusion partner from the desired protein. The fusion partner may be linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.). Fusion protein expression systems are also described in U.S. Pat. Nos. 5,227,293 and 5,358,857.

A further aspect of the invention is a DNA coding for a precursor as described above.

Likewise an aspect of the invention is a vector comprising a DNA coding for a precursor as described above, preferably wherein the vector is an expression vector suitable for expression in host cell such as $E.\ coli$. Such vectors include PET vector systems (Stratagene), pSE vector systems (Invitrogen), and PROLar vector systems (Clonentech).

A further aspect of the invention is a host cell such as $E.\ coli$ comprising a vector as described above. Suitable host cells are well known to the skilled artisan.

A further aspect of the invention is a process for the preparation of a precursor as described above, where (a) a DNA as described above is introduced into a vector as described above;

(b) the vector from (a) is introduced into a host cell;

(c) the host cell from (b) comprising the vector from (a) is used for expression: and (d) the precursor is isolated from the culture supernatant.

Preferably, the host is $E.\ coli$.

An additional aspect of the invention is a process for preparing a DNA as described above, where (a) this DNA is produced starting from the cDNA of human or monkey insulin by means of PCR and other molecular biology techniques, and (b) is isolated.

A further aspect of the invention is a process for preparing human insulin or an insulin analog, where (a) a precursor as described above is produced by the process as described above;

(b) the precursor from (a) is folded under suitable conditions so that the disulfide bridges can form as in human insulin, and the RDVP-$Y_n$ part and, where appropriate, the fusion portion Fus is deleted enzymatically; and (c) the human insulin or the insulin analog is purified.

A further aspect of the invention is the use of a precursor as described above for preparing insulin or an insulin analog, preferably where the preparation of insulin or an insulin analog takes place by the process as described above.

It is a further aspect of the invention to use a DNA as described above for preparing a precursor as described above.

One aspect of the invention is also the use of a vector as described above for preparing a precursor as described above.

A further aspect of the invention is the use of an $E.\ coli$ cell as described above for preparing a precursor as described above. Suitable $E.\ coli$ strains are, for example, BL 21, HB101, TOP10F (all from Invitrogen), DH5alpha (Clonentech), TOPP, JM109 (both from Stratagene).

The invention is now explained in detail by means of examples without, however, being restricted thereto.

EXAMPLES

Example 1

Expression of Proinsulin Derivatives

The expression takes place as described in EP-B1 0 489 780. In this case it is possible to introduce modifications on fermentation in large volumes. However, always the same conditions are maintained for comparing the expression rates.

The following general fermentation formula applies to operations on larger scales, which is described by way of example for a volume of 7.5 liters:

| | |
|---|---|
| fermentation volume | 7.5 l |
| sterilization conditions | 121° C., 20 minutes, at pH 3.5, adjusted to 7.0 with $NH_3$ after sterilization. |
| fermentation temperature | 37° C. |
| pH control | pH 7.0, adjustment with 25% aqueous ammonia |
| stirrer speed | 1500 rpm |
| aeration | 15 Sl/min (2 vvm) |
| duration | about 24 h |
| feeding | 65% glucose solution was metered in at a constant rate of 12 $gl^{-1}\ h^{-1}$ when the OTR reached 200 $mmol^{-1}\ h^{-1}$. |
| preculture | a shake culture was inoculated with a seed ampule and incubated at 37°C., 250 rpm for 3–4 h until the OD $A_{540}$ was ~1. |
| inoculation | the fermentors were inoculated with about 40 ml of preculture. |
| induction | at an $A_{540}$ of ≧40 with 40 mg/l (300 mg/fermentor) indolepropionic acid dissolved in about 10 ml of an aqueous $Na_2CO_3$ solution (with 0.17 g of $Na_2CO_3$). |

The meanings here are Sl = standard-conditions liter, vvm = volume/volume/minute and OTR = oxygen transfer rate.

Fermentation Media:

| | Amount g/l |
|---|---|
| Formula number GAI 100/95-000: | |
| Glucose 1-hydrate, D(+) min. 80% | 44 |
| Citric acid 1-hydrate | 3.48 |
| Ammonium sulfate min. 95% | 6.0 |
| Phosphoric acid, ortho, 85% | 2.99 |
| Dipotassium hydrogen phosphate | 1.18 |
| Sodium sulfate | 3.0 |
| Magnesium sulfate 7-hydrate, minimum 98% | 2.0 |
| Iron(III) sulfate × $H_2O$ | 0.5 |
| Trace element solution: RL 1/85-000 | 1.0 ml |
| Thiamine HCl | 0.005 |
| Desmophen 3600 | 0.5 |

-continued

| | Amount g/l |
|---|---|
| Trace element solution: RL 1/85-000 | |
| Copper(II) sulfate 5-hydrate | 1.6 |
| Potassium iodide | 4.0 |
| Ammonium molybdate 4-hydrate | 8.0 |
| Manganese(II) sulfate 1-hydrate | 12.3 |
| Zinc sulfate 7-hydrate | 16 |
| Boric acid | 20 |
| Amount in the shaken flask: | |
| Yeast extract | 8.0 |
| Glucose | 1.0 |
| NaCl | 3.5 |
| $KH_2PO_4$ | 1.32 |
| $K_2HPO_4$ | 3.68 |

Example 2

Preparation of Insulins

Insulins were produced according to the methods described and/or discussed in EP-B1 0 489 780 or EP-A 0 885 961. The preferred method for folding and purifying the respective fusion protein is the method as described in EP-B1 0 668 282 (see example 2). In this method, the preparation can be filtered according to the method as described in EP-A 0 288 809 before the purification is continued.

Example 3

Construction of the Plasmid pINT358d Coding for the C-chain derivatized human proinsulin B-RDVP $C_{11-35}$-A The plasmid was prepared using the primers Tir and Insu11 described in EP-B1 0 489 780. In addition, two new primer sequences were synthesized.

Primer PINT358fIII has the following sequence:

5'-CCC AAG ACC CGC GAT GTT CCT CAG GTG GAG CTG GGC GGG GGC CCT-3' (SEQ ID NO.:3)
B28 B29 B30 Arg Asp Val Pro C11 C12 C13 C14 C15 C16 C17 C18

Th bolded sequence indicates codons encoding newly introduced amino acids as compared to the cDNA, namely monkey insulin cDNA.

Primer PINT358revII has the sequence:

5'-CAGCTCCACCTGAGGAACATCGCGGGTCTT GGGTGTGTAG-3' (SEQ ID NO.: 4)

A PCR is carried out in accordance with EP-B1 0 489 780 with each of the primer pairs Tir/PINT358revII and Insu11/PINT358fIII and with DNA of the plasmid pINT90d as template. Aliquots of the products of the two reactions were combined and employed together with the primer pair Tir/Insu 11 in a third PCR. The product of this reaction is double-digested with the enzymes SalI/NcoI, and the product of this restriction digestion is, after purification, inserted into the vector DNA, opened with NcoI/SalI, of the plasmid pINT91d, which is likewise described in EP-B1 0 489 780. The plasmid constructed in this way is called pINT358d. The structure is confirmed by DNA sequence analysis. Competent E.coli cells are transformed with DNA of the plasmid. Expression of the proinsulin in bacteria takes place as in Example 1. After folding as in Example 2, the proinsulin is converted enzymatically into insulin and purified further as described in EP-B1 0 347 781. It is moreover possible by comparison with the method derived from pINT90d to collect in addition a marginal fraction in the ion exchange chromatography step, because this is not contaminated with Arg(B31)-insulin.

Example 4

Construction of the Plasmid pINT362d for Preparing Lys(B3)Glu(B29)-RDVP-$C_{11-35}$-proinsulin Needed for construction of the plasmid are DNA of the plasmids pINT329d and pINT358d as template and the primers Tir and Insu 11. In addition, two new primers Salforward and 329rev are synthesized. Primer Salforward has the sequence:

5'-TACACACCCGAGACCCGCGATGTTCCTCAGG-3' (SEQ ID NO.: 5)

The sequence section printed bold therein indicates the sequence which hybridizes with the plasmid pINT358d, while the remaining part is homologous with sequences of the B chain-encoding section of the plasmid pINT329d.

Primer 329rev has the following sequence:

5'-CCTGAGGAACATCGCGGGTCTCGGGTGTG TAG-3' (SEQ ID NO.:6)

The section printed bold therein indicates the region which is homologous with the antisense strand which describes the end of the B chain and the triplet for arginine in the plasmid pINT329d. The remaining sequence hybridizes with plasmid pINT358d. Two PCR runs are carried out. In these, the DNA of the plasmid pINT329d serves as template for the primer pair Tir/329rev and pINT358d DNA serves as template for the pair Salforward/Insu11.

Both reactions result in fragments which overlap by the sequence of the primer Salforward. It is thus possible to combine the two fragments in a third PCR and, with the aid of the primers Tir and Insu11, join them to give a DNA sequence which encodes the insulin analog. This reaction product is cleaved with the restriction enzymes NcoI/SalI and then inserted into the pINT91d vector fragment opened with SalI/NcoI. Competent cells of the E.coli strain K12 MM294 are transformed with the appropriate ligation mixture. Plasmid DNA is isolated from transformants and characterized. The correct plasmid is called pINT362d.

The crude yield of fusion protein after expression is found to be comparable to pINT90d. However, the folding yield is found to be about 40% better than with pINT329d.

The structure of the fusion protein encoded by pINT362d is as follows:

| MATTSTGNSAR | FVKQHLCGSHLVEALYLVCGERGFFYTPET | RDVPQVELGGGPG | |
|---|---|---|---|
| Fusion portion | B chain | C chain | |
| AGSLQPLALEGSLQKR | GIVEQCCTSICSLYQLENYCN | | (SEQ ID NO.: 7) |
| C chain (conc.) | A chain | | |

Example 5

Construction of the Plasmid pINT349d for Preparing His(B31) His(B32) Gly(A21)-RDVP-C$_{11-35}$-proinsulin Firstly the plasmid pINT140d whose DNA encodes the insulin analog Gly (A21) insulin is prepared.

Needed for this are two oligonucleotides to be used as primers in a PCR: oligonucleotide Tir is used as sense and oligonucleotide 140drev is used as antisense primer:

```
140drev   5'- AAAGGTCGACTATTAGCCGCAGTA -3'      (SEQ ID NO.: 8)
              Stop Stop Gly Cys Tyr             (SEQ ID NO.: 9)
                   A21 A20 A19
```

The two primers are employed in a standard PCR with DNA from the plasmid pINT90d. The reaction product is reacted as described in EP-B1 0 489 780 with the restriction enzymes NcoI and SalI and then inserted into the correspondingly opened vector pINT69d. The result is the plasmid pINT140d which is reisolated after transformation into *E. coli* K12 MM294 and is characterized by restriction and sequence analysis.

Two PCR runs are carried out starting from the DNA of the plasmid pINT140d. The first reaction uses the primer Tir and, as reverse primer, PINT349a with the following sequence:

```
    Val Gln Pro Val Asp Arg His His Thr Lys Pro Thr Tyr      (SEQ ID NO.: 10)
5'- CACCTGAGGAACATCGCGGTGGTGGGTCTTGGGTGTGTAG - 3'            (SEQ ID NO. 11)
    C12 C11  *   *   *   *   *   *  B30 B29 B28 B27 B26
```

The sequences therein marked with an asterisk designate the codons for the newly inserted amino acids.

The second PCR was carried out with the primers Inu11 and PINT349b.

Primer PINT349b has the sequence:

```
     Pro Lys Thr His His Arg Asp Val Pro Gln Val Glu Leu    (SEQ ID NO.: 12)
5' - ACCCAAGACCCACCACCGCGATGTTCCTCAGGTGGAGCTG - 3'          (SEQ ID NO.: 13)
     B28 B29 B30  *   *   *   *   *   *  C11 C12 C13 C14
```

From position 34 to position 1 of the DNA sequence, the primer is complementary to PINT349a. It is therefore possible to join the reaction products from the two PCRs in a third PCR with the primers Tir and Insu 11 to give the DNA fragment which codes for the required proinsulin derivative. The product of this reaction is reacted as described with the enzymes NcoI und SalI and inserted into the pINT91d vector fragment opened with the enzymes and transformed into *E. coli* K12. After characterization of the plasmids from transformants, the correct plasmid constructs are called pINT349d.

Expression of the fusion protein shows a distinct increase in the yield of fusion protein. The yield is surprisingly about 20% higher than can be achieved with pINT90d and is about 5 times greater than achieved with the plasmid pINT30d. The folding rate is moreover comparable with the rate achieved with the monkey preproinuslin encoded by pINT90d.

The German Priority Document, DE 19947456.7, filed Oct. 2, 1999, is expressly incorporated herein by reference in its entirety. All references cited herein, including U.S. and foreign patent applications, are expressly incorporated herein by reference in their entirety.

What is claimed is:

1. A precursor of human insulin or of an insulin analog of the formula I:

$$\text{Fus-B}(1\text{-}30)\text{-RDVP-Yn-A}(1\text{-}21) \qquad (I),$$

wherein Fus is an optionally present fusion portion, B(1-30) is a B chain of human insulin, Y is an amino acid chain which terminates with a basic amino acid at the C terminus, n is from 2 to 50 and indicates the length of the amino acid chain Y, and A(1-21) is an A chain of human insulin, wherein the A chain and/or the B chain can be modified by amino acid substitutions, deletions and/or additions with the biological activity of insulin being preserved.

2. A precursor as claimed in claim 1, wherein $Y_n$ is amino acids 5 to 35 of a C peptide of human or monkey insulin.

3. A precursor as claimed in claim 1, wherein Yn is amino acids 11 to 35 of a C peptide of human insulin.

4. A precursor according to claim 1, wherein the B chain of human insulin comprises: Lys(B3)Glu(B29).

5. A precursor according to claim 1, wherein the A chain of human insulin comprises Gly(A21) and the B chain of human insulin comprises two additional amino acids adjacent to B(30): His(B31) and His(B32).

6. A DNA coding for a precursor according to claim 1.

7. A vector comprising a DNA as claimed in claim 6.

8. A vector as claimed in claim 7, wherein the vector is an expression vector suitable for expression in a host cell.

9. A host cell comprising a vector as claimed in claim 8.

10. The vector of claim 8, wherein the host cell is *E. coli*.

11. The host cell of claim 9, wherein the host cell is *E. coli*.

12. A process for preparing a precursor according to claim 1, comprising the steps of:

a) introducing a DNA coding for a precursor according to claim 1 into a vector;

b) introducing the vector from (a) into a host cell;

c) allowing the host cell to express the precursor into a culture supernatant; and d) isolating the precursor from the culture supernatant.

13. A process for preparing human insulin or an insulin analog, comprising the steps of:

a) preparing a precursor by the process as claimed in claim 12, b) forming disulfide bridges in the precursor by allowing the precursor from (a) to fold;

c) optionally enzymatically cleaving the fusion portion Fus; and c) purifying the human insulin or the insulin analog.

14. The process of claim 12, wherein the host cell is *E. coli*.

* * * * *